(12) United States Patent
Perricone

(10) Patent No.: US 7,226,608 B2
(45) Date of Patent: *Jun. 5, 2007

(54) TOPICAL USE OF MICROFINE CALCINED ALUMINA

(75) Inventor: Nicholas V. Perricone, Meriden, CT (US)

(73) Assignee: N.V. Perricone LLC, Meriden, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/197,889

(22) Filed: Aug. 5, 2005

(65) Prior Publication Data

US 2005/0271607 A1    Dec. 8, 2005

Related U.S. Application Data

(63) Continuation of application No. 10/269,581, filed on Oct. 11, 2002, now Pat. No. 7,037,512.

(51) Int. Cl.
*A61K 7/00* (2006.01)
*A61K 7/06* (2006.01)
*A61K 9/14* (2006.01)
*A61K 33/26* (2006.01)
*A01N 25/00* (2006.01)

(52) U.S. Cl. .................... 424/401; 424/70.1; 424/400; 424/405; 424/417; 424/489; 424/646; 424/649; 424/682; 424/688; 424/690; 424/691

(58) Field of Classification Search .......... 424/59, 424/400, 405, 417, 489, 646, 649, 682, 688, 424/690, 691
See application file for complete search history.

(56) References Cited

U.S. PATENT DOCUMENTS

| 4,801,445 | A | 1/1989 | Fukui et al. ............... 424/69 |
| 4,822,600 | A | 4/1989 | Wortzman ................ 424/59 |
| 5,468,471 | A | 11/1995 | Zecchino et al. .......... 424/59 |
| 6,235,270 | B1 | 5/2001 | Ishii et al. ................ 424/59 |
| 6,261,713 | B1 | 7/2001 | Walele et al. ............. 429/54 |
| 7,037,512 | B2 * | 5/2006 | Perricone .................. 424/401 |

* cited by examiner

*Primary Examiner*—Johann Richter
*Assistant Examiner*—Konata M. George
(74) *Attorney, Agent, or Firm*—St. Onge Steward Johnston & Reens LLC

(57) ABSTRACT

Dispersions containing from about 0.5% to about 30% by weight dispersed microfine calcined alumina, stainless steel, or gold particles typically having particle size of less than about 5µ, more narrowly 1µ or less, suspended in a cosmetically acceptable carrier are useful as sunblocks for skin and hair while simultaneously providing treatments that render skin and hair smoother, more uniform, lustrous, visually appealing and healthier-looking.

20 Claims, No Drawings

TOPICAL USE OF MICROFINE CALCINED ALUMINA

CROSS REFERENCE TO RELATED APPLICATIONS

The present application is a continuation of U.S. patent application Ser. No. 10/269,581 filed 11 Oct. 2002 and entitled "Topical Use of Microfine Calcined Alumina" now issued as U.S. Pat. No. 7,037,512.

FIELD OF THE INVENTION

This invention relates to novel organic dispersions of ultra-fine calcined alumina, or other ultrafine medical grade inert particles such as stainless steel or gold, that are suitable for use in sunblock and cosmetic preparations for skin and hair.

BACKGROUND OF THE INVENTION

It is now known that a variety of skin diseases and conditions in which the skin has undergone some form of damage can be exacerbated by, or traced directly or indirectly to, solar radiation exposure, as is damage to hair. Such is the case, for example, in ultraviolet-induced skinburn and accelerated skin aging caused by sunlight. Continued sun exposure can lead to pre-cancers and cancers, including melanoma. Hence, there is currently considerable public health and cosmetic interest in the promotion of sunscreen and sunblock products for use on exposed skin surfaces.

Conventional sunscreens are typically prepared by suspending or dissolving an organic compound that absorbs and/or attenuates harmful ultraviolet (UV) radiation, such as, for example, oxybenzone(2-hydroxy-4-methoxybenzophenone), doxybenzone(2,2')-dihydroxy-4-methoxybenzophenone), aminobenzoic acid, cinoxate(2-ethoxyethyl-p-methoxycinnamate), diethanolamine-p-methoxycinnamate, digalloyltrioleate ethyl-4-bis(hydroxypropyl)aminobenzoate, 2-ethylhexyl salicylate, glyceryl aminobenzoate, homosalate(3,3,5-trimethylcyclohexyl salicylate, triethanolamine salicylate, 2-phenylbenzimidazole-5-sulfonic acid, sulisobenzone(2-hydroxy-4-methoxybenzophenone-5-sulfonic acid), Padimate A (amyl p-dimethylaminobenzoate), Padimate O (octyl dimethyl p-aminobenzoate), 4-t-butyl-4'-methoxydibenzoylmethane, the combination of 2-hydroxy-1,4-naphthoquinone with dihydroxyacetone and methyl anthranilate, in a cosmetically acceptable lotion, oil, cream, or emulsion.

Sunblocks, in contrast, generally contain an inorganic compound that reflects the sun's rays. The best known sunblock is zinc oxide, first formulated as a thick white cream famous on the noses of well-tanned lifeguards, but less obvious tinted zinc oxides and more user-friendly variations containing, instead, titanium dioxide, calamine, and fumed silica suspended in a cosmetically acceptable carrier have been described. (See, for example, U.S. Pat. No. 4,801,445 to Fukui, et al., and U.S. Pat. No. 4,822,600 to Wortzman; these and patents cited hereafter are incorporated herein in their entireties by reference.)

Since different organic compounds used as active ingredients in sunscreens absorb radiation of different wavelengths and with different efficiencies, sunscreens are unequal in their protection from both UVA and UVB rays. In addition, few sunscreens protect against visible or infrared (IR) radiation, which penetrate deeper than UV rays and can also cause damage. Therefore, the most effective protection against irradiation by the sun is provided by sunblocks, as these protect against radiation at all wavelengths. However, many sunblocks containing dispersed powdered inorganics such as zinc oxide and titanium dioxide are esthetically displeasing in that they spread poorly and have an unpleasant heavy and draggy feel when applied to the skin, and, since they are pigments, they can leave a white/blue residue, particularly at higher concentrations. Even when micromilled to ultra-micro particle sizes of $0.01\mu$ to $0.15\mu$, titanium dioxide agglomerates into clumps of much higher particle sizes that are unacceptable for cosmetic use. Various dispersing agents and powder pretreatments have been suggested to improve the characteristics of formulations containing these sunblock inorganics such as coating the particles with vegetable oils, mineral oil, fatty acid esters or salts, phospholipids, silicone polymer films, branched chain organics, and the like. (See, for example, Fukui, et al., and Wortzman cited above, and U.S. Pat. No. 5,468,471 to Zecchino, et al., and other disclosures reviewed in these patents.) It would be beneficial to have alternative sunblocks exhibiting more desirable properties.

SUMMARY OF THE INVENTION

This invention is based upon the finding that microfine calcined alumina can be dispersed in topical compositions that not only act as sunblocks, but also mask skin imperfections such as wrinkles, scars, and enlarged pores on skin, and structural flaws on the cylindrical keratinous exteriors of hair shafts. While not wishing to be bound to any theory, ultrafine calcined alumina particles seem to function like small mirrors on the surface of the skin or hair. They reflect back incident radiation, functioning as a sunblock. At the same time, particles that have silted into skin and exterior hair shaft imperfections smooth the surfaces so that the incident light reflected back is less scattered, so that flaws become less apparent visually. Pronounced skin and hair protection and cosmetic benefits are achieved.

It is thus an objective of this invention to provide alternate sunblock compositions for skin and hair. It is another objective to provide topical compositions that increase the smoothness and surface uniformity of skin and hair to which they are applied. It is a further and important objective of the invention to provide methods of protecting skin against the deleterious effect of sun exposure while simultaneously masking wrinkles, scars, pits, enlarged pores, and other skin imperfections by applying a topical composition to exposed skin areas. It is also a related objective to provide corresponding compositions that protect hair from radiation-induced damage, and render individual hairs smoother, more manageable, and shiny.

These and other objectives are accomplished by the present invention, which provides emulsions of dispersed microfine calcined alumina, stainless steel, and/or gold particles which typically have a particle size of about $25\mu$ or less, preferably about $10\mu$ or less, and even more preferably about $5\mu$ or $1\mu$ or less, suspended in a cosmetically acceptable carrier. Typical emulsions contain from about 0.5% to about 30%, more narrowly from about 5% to about 25% dispersed particles suspended in a cosmetically acceptable carrier. As illustrated hereafter, formulations containing from about 3% to about 10% by weight particles in waterproof and film-forming silicone base carriers exhibited a variety of desirable properties for topical application to the skin. Exemplary hair compositions are formulated as rinses.

Also encompassed by the invention are methods of using microfine dispersed particulate emulsions to protect mammalian skin or hair from ultraviolet and infrared radiation (especially the former), and to render skin and hair more uniform and smoother by topical application of dispersions of the invention.

In the practice of this invention, dispersions of microfine calcined alumina, stainless steel, or gold particles in a cosmetically acceptable carrier are prepared and applied topically to mammalian skin or hair. When so applied, the dispersions act as a sunblock, protecting the skin and hair from ultraviolet and infrared radiation. Microfine particulate dispersions also render skin and hair more uniform and smoother, more lustrous, and healthier-looking.

As used herein, the terms "ultra-fine" and "microfine" are used synonymously. Preferred microfine particles useful in preparing formulations of the invention have a particle size of less than about 25μ, typically less than about 10μ, preferably less than about 5μ, and even more preferably less than about 1μ. Useful particles include microfine calcined alumina, stainless steel, gold, or mixtures of these. A preferred embodiment illustrated hereafter employs calcined alumina having a particle size of 1μ or less. By "calcined alumina" is meant alumina, which is aluminum oxide, $Al_2O_3$, sometimes also called "α-corundum", that has been heated to a high temperature, often above 1000° C., to expel volatile impurities such as soda found in crude metal oxide samples. By "stainless steel" is meant a tough, elastic alloy of iron with carbon containing nickel, chromium, or both, that is hard and does not tarnish. Very fine specialty grades of calcined alumina, stainless steel and gold are available commercially for a variety of uses, particularly as refractories. High quality, pure medical grade particles are preferred, as well as dental grade calcined alumina or gold. Indeed, it is an advantage of the invention that calcined alumina, stainless steel, and gold are castable refractories that have been used in medical and dental implant devices and on implant surfaces and shown to be extremely stable, chemically inert, non-toxic, non-irritating, and non-sensitizing, as is dental grade calcined alumina used in toothpastes, mouth washes, polishing agents, tooth coatings, and the like. Medical grade calcined alumina particles were used in the examples that follow.

The microfine particles are dispersed in a cosmetically acceptable carrier to form a suspension, an emulsion, or a microemulsion for topical application to the skin or hair. Microemulsions are preferred. By "cosmetically acceptable carrier" is meant a carrier that is inert and does not bring about any adverse effect on the skin or hair to which it is applied. Carriers are typically lotions, creams, ointments, soaps, and the like conventionally used in dermatology to facilitate topical application, particularly carriers which will form a film or layer on the skin or hair to which it is applied so as to localize the application and provide some resistance to washing off by immersion in water or by perspiration, while simultaneously serving as a sunblock. Many preparations are known in the art and formulated using conventional techniques, and include lotions containing oils and/or alcohols and emollients vegetable oils, hydrocarbon oils and waxes, silicone oils, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels by utilization of different proportions of the ingredients and/or by inclusion of thickening agents such as gums or other forms of hydrophilic colloids. By the same token, hair formulations are typically shampoos, rinses, and gels rather than lotions or creams, but contain the same general ingredients suitable for dermatological use.

Some preferred embodiments for topical use on skin illustrated below employ one or more water-proof, film-forming silicone bases shown to be safe in sunscreens and cosmetics. A variety of these products are available commercially, and include silicones as well as copolymers of silicones, dimethylsilicones, siloxane, or siloxone with cetyl or other alkyl, or cyclohexyl derivatives, such as, for example (but not limited to), methicone, dimethicone, cetyidimethicone, cetyldimethicone copolyol, cyclomethicone, polydimethylsiloxane, and mixtures of these. An emulsion is formed by mixing and/or milling the particles in the carrier, with optionally other ingredients such as those set out below. Insofar as has been determined based upon clinical studies to date, no adverse side effects are encountered.

Topical dispersions of the invention can comprise additional ingredients shown to be beneficial to skin and/or hair when topically applied, particularly ingredients shown to be beneficial for the prevention of radiation-induced skin or hair damage, and ingredients commonly found in skin and/or hair care compositions and cosmetics, such as, for example, tinting agents, emollients, conditioning agents, emulsifying agents, humectants, preservatives, antioxidants, perfumes, chelating agents, etc. Compounds that enhance the SPF of sunscreens such as $C_{12}$ and $C_{14}$ alkyl benzoates, e.g., Finsolv TN™, may also be added to sunblocks of the invention.

Preservatives include, but are not limited to, $C_1$–$C_3$ alkyl parabens and phenoxyenthanol, typically present in an amount ranging from about 0.5% to about 2.0% by weight percent, based on the total composition. Emollients, typically present in amounts ranging from about 0.01% to 5% of the total composition include, but are not limited to, fatty esters, fatty alcohols, mineral oils, polyether siloxane copolymers, and mixtures thereof. Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts from about 1% to about 10% by weight of the composition, include, but are not limited to, stearic acid, cetyl alcohol, stearyl alcohol, steareth 2, steareth 20, acrylates/$C_{10-30}$ alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof. Antioxidants, typically present in an amount ranging from about 0.02% to about 0.5% by weight of the composition, include, but are not limited to, butylated hydroxy toluene (BHT); butylated hydroanisole (BHA); phenyl-α-naphthylamine; hydroquinone; propyl gallate; nordihydroquiaretic acid; green tea extracts; mixed polyphenols; and mixtures of any of these.

Buffering agents are employed in many compositions. Preferably, the amount of buffering agent is one that results in compositions having a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

It is an advantage of the invention that the microfine particulate compositions are virtually transparent when applied to skin or hair. The particles are so fine that emulsions have a good feel and are easy to apply. As a sunblock, preferred embodiments exhibit an SPF (sun protectant factor) of at least about 15, preferably about 25 to 30, and in some cases over about 45. Broad spectrum radiation is reflected, offering excellent protection against radiation at all wavelengths, including shielding against both UVA and UVB ultraviolet radiation, as well as visible and infrared. Rough skin and hair scatters light in a manner which emphasizes openings and imperfections, so application of micro-particulate emulsions of the invention simultaneously provides more healthy-looking and lustrous skin and hair. The deposited particles fill enlarged pores, skin pits, and scars, and smooth wrinkles, ridges, scars, and other skin blemishes, providing a smoother, flatter surface for light reflection, so that skin appears much less imperfect and more appealing visually. Dispersions of the invention are useful in a variety of cosmetics, including foundations, eyeshadows, lipsticks, facial powders, and the like. Similarly, hair treated with dispersions of the invention becomes not only physically smoother, but softer, shinier and more manageable. The particles and the carrier are inert, so no adverse reactions are observed.

EXAMPLES

Two batches of medical grade calcined alumina having a primary particle size of 1μ or less were used in the nonlimiting examples that follow. Chemical analysis of one lot yielded an $Al_2O_3$ content of 99.60%, 0.42% $Na_2O$, and 0.01% $Fe_2O_3$ by weight; the other lot had an $Al_2O_3$ content of 99.50% by weight, 0.44% $Na_2O$ and and 0.01% $Fe_2O_3$. The percentages are based on weight.

Example 1

Three sunblocks were prepared by emulsifying the following ingredients, in amounts expressed as % w/w:

| Ingredient | A | B | C |
|---|---|---|---|
| Water | Q.S. to 100.00 | | |
| EDTA-Na$_2$ | 0.10 | 0.10 | 0.10 |
| Sodium Chloride | 0.80 | 0.80 | 0.80 |
| Aloe-Vera 200:1 | 0.05 | 0.05 | 0.05 |
| Isopropylpalmitate | 10.00 | 5.00 | 10.00 |
| Finsolve TN ™ | 5.00 | 5.00 | 5.00 |
| ABIL We-09 | 6.00 | 6.00 | 6.00 |
| Cetyldimethicone | 2.00 | 2.00 | 2.00 |
| Cetyldimethicone Copolyol | 1.75 | 1.75 | 1.75 |
| Beeswax | 1.20 | 1.20 | 1.20 |
| Vitamin E Acetate | 0.10 | 0.10 | 0.10 |
| Permethyl 99A | — | — | 0.50 |
| Germaben IIE ™ | 0.50 | 0.50 | 0.50 |
| Calcined Alumina | 10.00 | 4.00 | 3.00 |

All three formulations exhibited good viscosity and flow characteristics, and were easy and pleasant to apply to the skin. Reactions by users were uniformly favorable.

Example 2

A foundation cream that gave the skin a smoother, more uniform appearance upon application, was prepared by emulsifying the following ingredients:

| Ingredient | % w/w |
|---|---|
| Purified water | Q.S. to 100.00 |
| Quaternium-15 | 0.20 |
| DHA-Na | 0.10 |
| Hyaluronic Acid-NA | 2.00 |
| Calcined Alumina | 3.00 |
| HDI/Trimethyloyl Hexyl Lactone | 15.00 |
| Polydimethylsiloxane | 4.50 |
| Mica/Dimethicone | 1.90 |

The formulation had the consistency of a soft cream, and spread luxuriously on the skin, rendering it visibly flatter and more perfect, and thus cosmetically much more attractive.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A sunblock composition comprising a dispersion of calcined alumina, stainless steel, or gold particles, or combinations thereof, having a particle size of less than about 25μ in a cosmetically acceptable carrier.

2. A dispersion according to claim 1 which has an SPF of at least about 15.

3. A dispersion according to claim 1 which has an SPF of at least about 25.

4. A dispersion according to claim 1 wherein the particle size is about 10μ or less.

5. A dispersion according to claim 4 wherein the particle size is about 5μ or less.

6. A dispersion according to claim 5 wherein the particle size is about 1μ or less.

7. A dispersion according to claim 1 comprising calcined alumina particles.

8. A dispersion according to claim 1 comprising stainless steel particles.

9. A dispersion according to claim 1 comprising gold particles.

10. A dispersion according to claim 1 wherein the carrier comprises a film-forming silicone.

11. A dispersion according to claim 10 wherein the carrier comprises a methicone.

12. A dispersion according to claim 1 comprising from about 0.5% to about 30% by weight particles.

13. A dispersion according to claim 12 comprising from about 5% to about 25% by weight particles.

14. A dispersion according to claim 13 comprising from about 5% to about 25% by weight calcined alumina particles having a particle size of about 1μ or less suspended in a cosmetically acceptable carrier containing a silicone.

15. A method of protecting mammalian skin or hair from radiation-induced skin damage comprising applying to exposed skin or hair an effective amount of a dispersion containing microfine calcined alumina, stainless steel, or gold particles in a cosmetically acceptable carrier.

16. A method according to claim 15 wherein the particles have a particle size of less than about 10μ.

17. A method according to claim 16 wherein the particles are calcined alumina.

18. A method according to claim 16 wherein the particles are stainless steel.

19. A method according to claim 16 wherein the particles are gold.

20. A method according to claim 16 wherein the dispersion comprises from about 0.5% to about 30% by weight particles.

* * * * *